United States Patent [19]

Smith

[11] 4,222,379

[45] Sep. 16, 1980

[54] MULTIPLE BLOOD BAG HAVING PLASTICIZER-FREE PORTIONS AND A HIGH BLOOD COMPONENT SURVIVAL RATE

[75] Inventor: Dale A. Smith, Barrington, Ill.

[73] Assignee: Baxter Travenol Laboratories, Inc., Deerfield, Ill.

[21] Appl. No.: 955,059

[22] Filed: Oct. 26, 1978

[51] Int. Cl.[2] .......... A61M 5/00; A61J 1/00

[52] U.S. Cl. .......... 128/214 D; 128/272

[58] Field of Search .......... 128/214 D, 214 R, 272, 128/DIG. 24; 260/31.8 XA

[56] References Cited

U.S. PATENT DOCUMENTS

| | | | |
|---|---|---|---|
| 3,186,961 | 6/1965 | Sears et al. | 260/31.8 R |
| 3,940,802 | 3/1976 | Sako et al. | 128/214 D |
| 3,945,380 | 3/1976 | Dabney et al. | 128/214 D |
| 3,986,506 | 10/1976 | Garber et al. | 128/214 D |
| 4,112,089 | 10/1978 | Grode et al. | 128/214 D |
| 4,140,162 | 2/1979 | Gajewski et al. | 150/1 |

OTHER PUBLICATIONS

"Reduction of Haemolysis During Perfusion During Collection and Storage of Blood in Plastic Bags", *The Lancet*, Jul. 16, 1960, p. 154.

*Primary Examiner*—William E. Kamm
*Assistant Examiner*—Thomas Wallen
*Attorney, Agent, or Firm*—H. W. Collins; Paul C. Flattery; Garrettson Ellis

[57] ABSTRACT

A multiple blood bag system comprising a donor bag for receiving blood from a donor, and one or more transfer bags, communicating by flexible tubing with the donor bag, for receiving a blood component from the donor bag. In accordance with this invention, the various bags may be made of differing materials to provide differing characteristics to the bags as desired. For example, the transfer bag or bags may be made of a translucent, flexible, sterilizable material which is free of blood extractable ester-type plasticizers, and may have a relatively high carbon dioxide diffusion capacity. The donor bag may be made of a translucent, flexible, sterilizable material which contains preferably at least five percent by weight of a specified ester plasticizer, sufficient to cause a substantial reduction in plasma hemoglobin produced by blood stored under normal conditions for 21 days in the donor bag, when compared with blood in a corresponding, plasticizer-free donor bag stored under equivalent conditions.

37 Claims, 1 Drawing Figure

Figure 1:
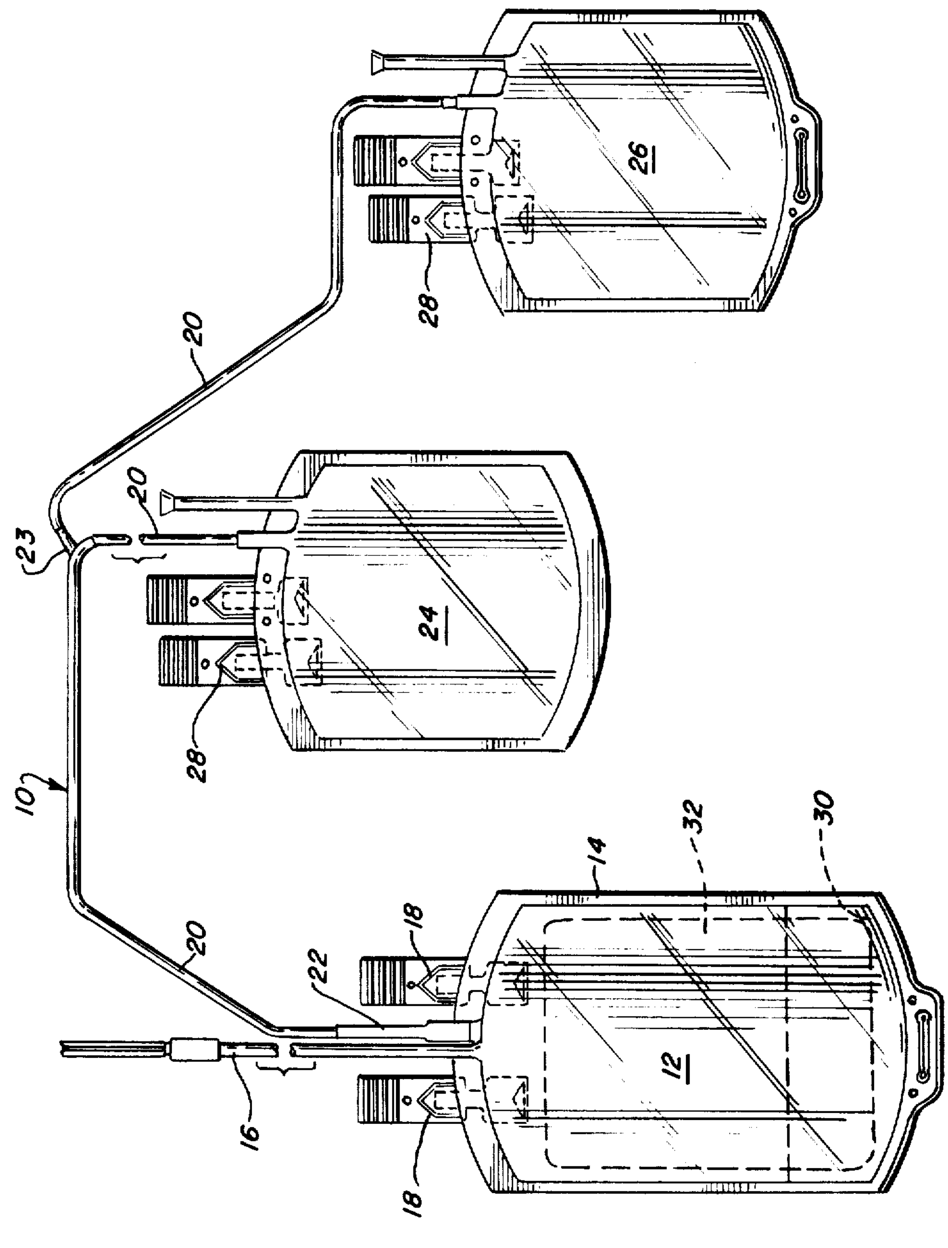

MULTIPLE BLOOD BAG HAVING PLASTICIZER-FREE PORTIONS AND A HIGH BLOOD COMPONENT SURVIVAL RATE

BACKGROUND OF THE INVENTION

Multiple blood bags are commercially available from the Fenwal Division of Baxter Travenol Laboratories, Inc., for collecting and processing blood under sterile conditions to obtain various blood components as may be desired, for example, packed red cells, plasma, platelets, and cryoprecipitate.

The currently-available blood bags are made of a polyvinyl chloride formulation, which includes, as an ester-type plasticizer, di-2-ethylhexylphthalate. This blood bag system has served extremely well in the storage and processing of blood and blood components, exhibiting a high survival rate, with a resultingly low plasma hemoglobin content after, for example, 21 days of storage.

However, some concern has been expressed from various sources about the potential undesirability of the plasticizer leaching from the plastic material, and entering the blood, from where it is infused to the patient upon infusion of the blood or blood components. This is so despite the lack of any apparent significant toxicity of the particular plasticizer used, the concern being about long-term and subtle effects not yet discovered.

Accordingly, various plastic formulations which are flexible, translucent, sterilizable, and free of liquid plasticizers capable of leaching have been tested as blood bag materials. Many of the plastic formulations which have been tested have physical characteristics which are different from each other and from the current polyvinyl chloride formulations. For example, some plastic formulations have an improved capacity to transfer carbon dioxide, so that it would be of advantage to make one or more of the transfer packs of a multiple blood bag of such a material to permit an increased diffusion rate of carbon dioxide through the transfer pack during platelet storage so that the pH decrease of the platelets during storage is reduced.

It has been surprisingly found that the presence of certain ester-type plasticizers such as di-2-ethylhexylphthalate and di-2-ethylhexyladipate in plastics causes a significant lowering of the plasma hemoglobin content during long-term storage of blood in containers made of such plastics.

Accordingly, in accordance with this invention, the overall contact of blood plasma and other components to the blood-extractable plasticizer may be minimized, while still attaining low plasma hemoglobin levels in long-term storage, by providing a multiple blood bag system in which the donor bag is made of a plastic which contains a blood extractable plasticizer, preferably a branched dioctyl phthalate ester plasticizer, but the transfer bags are free of blood extractable plasticizers. Accordingly, the red blood cells, which normally are retained in the donor bag, are stabilized and preserved by the surprising benefit which has been found by the presence of the specific plasticizers described above. At the same time, the plasma and other blood components may be removed from the donor bag, being thus freed from further exposure to the plasticizer, and stored in transfer bags of different materials of different desirable characteristics, for example, transfer bags made of a material having relatively high carbon dioxide diffusion capability.

Accordingly, in accordance with this invention, the specific properties of the various bags of the multiple blood bag of this invention may be optimized by the use of different materials for each of the bags as desired, with one bag material being chosen for the donor bag in order to minimize the formation of plasma hemoglobin and to maximize the life of the red cells, while the transfer packs may be made of material having other characteristics, for example, the relatively high carbon dioxide diffusion capability.

DESCRIPTION OF THE INVENTION

The multiple blood bag system of this invention comprises a donor bag for receiving blood from a donor, and at least one transfer bag for receiving a blood component from the donor bag. The donor bag and transfer bag are connected together by conduit means providing sealed flow communication between them.

In accordance with this invention, the donor bag and transfer bag may be made of plastic materials which each comprise a different polymer entity so that the respective bag materials exhibit different characteristics which may be specifically selected for beneficial effect in the specific function of each of the transfer and donor bags.

For example, the transfer bag or bags may be made of a translucent, flexible, sterilizable material which is free of blood-extractable plasticizers. On the other hand, the donor bag may be made of a transparent, flexible, sterilizable material which contains an amount of blood-extractable plasticizer selected from the group consisting of dioctylphthalates and dioctyladipates, preferably di-2-ethylhexylphthalate, and preferably in a concentration in the flexible material of 5 to 50 weight percent, and typically about 15 to 40 weight percent.

This can result in a substantial reduction in plasma hemoglobin produced by blood stored under normal conditions for 21 days in the donor bag, when compared with blood in a corresponding donor bag, free of blood extractable plasticizers and stored under equivalent conditions.

If desired, only portions of the bag materials which are in contact with the blood contained therein may contain the blood-extractable plasticizers of this invention, although preferably the entire bag material contains the plasticizer. Alternatively, a plastic insert member such as a sheet of plastic or the like positioned within the blood bag may contain the blood-extractable plasticizer material, while the actual bag walls may be relatively free of plasticizer. Both of these circumstances are generally equivalent to the preferred use of blood-extractable plasticizer throughout essentially the entire material of the donor bag.

It is specifically desirable for the concentration and configuration of plasticizer in the bag to be such that when the bag is filled with blood and stored on a long term basis, the concentration of the blood-extractable plasticizer in the blood rises to typically about 30 to 100 micrograms per ml., and preferably from about 50 to 80 micrograms of the plasticizer per ml., in the blood in 21 days. This takes place due to the extraction of the plasticizer from the plastic material in dissolved form into the blood.

It has been found to be difficult to dissolve the blood-extractable plasticizers used herein in bulk in the blood, and it has been found that a greater beneficial effect is provided by placing the extractable plasticizer in the plastic material of the blood bag for extraction by the blood during the storage period.

The transfer bag or bags and optionally the tubing in the blood bag of this invention may be made of a polyester material in accordance with the teachings of U.S. Pat. No. 4,045,431.

It may also be desirable to make the donor bag of the multiple bag system of this invention out of a similar polyester material to the transfer bag, but containing blood-extractable plasticizer.

Alternatively, bags of this invention may be made out of a blood-compatible polyurethane formulation.

Another type of material which is suitable for the transfer bag of this invention comprises a mixture of from 10 to 40 percent by weight of a polyolefin consisting essentially of propylene units; from 40 to 85 percent by weight of a block copolymer, having thermoplastic rubber characteristics, consisting essentially of (1) a central block comprising 50 to 85 percent by weight of the copolymer molecule of a rubbery olefin polymer (and preferably consisting of generally equal proportions of ethylene and butylene units); and (2) terminal blocks of polystyrene; and as a third, optional ingredient, from 0 to 40 percent by weight of a softening agent such as polyethylene or poly(ethylene-vinyl acetate) containing no more than 35 percent by weight of vinyl acetate units. This polyolefin formulation exhibits relatively good low temperature strength and good carbon dioxide transfer characteristics, and thus is suitable for use as transfer bags for collecting cryoprecipitate or storing platelets.

The above material is further described in U.S. patent application Ser. No. 819,924 filed July 28, 1977 now U.S. Pat. No. 4,140,162.

The above block copolymer is commercially available from the Shell Chemical Company under the trademark KRATON or KRATON-G, the latter class of materials being preferred.

Other materials from which the transfer bags of this invention, and optionally the tubing, may be made include poly(ethylene-vinyl acetate) copolymers, and polyethylene formulations, all of the above material being preferably essentially free of the blood-extractable plasticizers.

The donor bag, as described above, contains a blood extractable liquid plasticizer as described above, the plasticizer being generally present in a concentration of 5 to 50 percent by weight of the overall plasticized plastic material making up the donor bag.

Preferably, a conventional formulation of polyvinylchloride, plasticized with a dioctyl phthalate such as di-2-ethylhexylphthalate, similar to present commercial formulations, may be used. Alternatively, other plastics such as a polyester bag formulation may be used, for example utilizing the above-described polyester, in which preferably from 15 to 40 percent by weight of the di-2-ethylhexylphthalate plasticizer is present, either by formulation along with the original plastic material, or by allowing the plastic to soak in the diethylhexylphthalate until the desired amount of plasticizer has been taken up by the material. Typically, the polyester formulation may contain about 20 percent by weight of the ester plasticizer.

Alternatively, di-2-ethylhexyladipate or an equivalent material may be used as the blood-extractable plasticizer.

Referring to the drawings, FIG. 1 is a plan view of a multiple blood bag system in accordance with this invention.

Blood bag system 10 includes a donor bag 12 which may be of conventional construction, being made of a pair of plastic sheets, being sealed at periphery 14, and containing a blood collection tube 16 having the usual donor needle, and a pair of access ports 18.

Transfer tubing 20 is connected to donor bag 12, for fluid flow through the transfer tubing, being controlled by conventional valving means 22, such as a cannula and diaphragm valve. Transfer tubing 20 communicates through Y site 23 to transfer bags 24, 26 which may also be of conventional construction, with the exception of the materials of which they are made, having the conventional access ports 28 and other known design features.

In accordance with this invention, transfer bags 24, 26 are made of a material which may be translucent (e.g., transparent), flexible, and preferably autoclavable to permit sterilization, being made of a material which is free of blood-extractable plasticizers, for example, a material as described above. Accordingly, plasma and other blood components which are expressed into transfer bags 24, 26 enter an environment free of additional exposure to plasticizers. In fact, the plasticizer-free formulations of bags 24, 26 can reduce the plasticizer level in the blood components by absorption thereof if the blood bag material of the transfer bags is of an appropriately plasticizer-compatible material.

It is specifically preferable for at least one of the transfer bags 24, 26 to be made of a material which has a relatively high capability to permit the diffusion of carbon dioxide, so that the bag may be desirably used as a platelet storage bag. Specifically, such a bag may be made from the polyolefin-thermoplastic rubber formulation described above and in the cited U.S. patent application Ser. No. 819,924, filed July 28, 1977, or other formulations described therein. Alternatively, the same transfer bag may be used to collect and store cryoprecipitate in view of its good low temperature strength.

The other of the two transfer bags may be made of the polyester formulation described above. Accordingly, one preferred embodiment the multiple bag shown in the drawings may comprise a pair of transfer bags 24, 26, each of which is made of a different material from the other. Alternatively, they may be the same.

Tubing 20 may be made of a flexible material, free of blood-extractable plasticizers, similar to that of one of the transfer bags 24, 26, if desired, or it may be made of the material of donor bag 12, or any other desired material.

Donor bag 12 is made of a transparent, flexible, preferably autoclavable material which contains the desired amount of blood-extractable plasticizer as described above, to cause a substantial reduction in the plasma hemoglobin of blood stored under normal conditions for 21 days in the donor bag 12, when compared with a corresponding extractable plasticizer-free donor bag stored under equivalent conditions.

As stated above, a commercial polyvinyl chloride blood bag formulation may be used, which contains di-2-ethylhexyl phthalate. Alternatively, another plastic such as a polyester material as described above, containing the desired amount of compatible liquid plasticizer, may be used.

If desired, an optional plastic insert 32 may be inserted within the donor bag 12. Insert 32 may be made of a similar material to donor bag 12, or a material which is particularly compatible to the desired blood-extractable plasticizer used herein. Accordingly, the material of bag 12 may be relatively free of the desired blood-extractable plasticizer, but insert 32 within the bag may carry any desired amount of the plasticizer, preferably from 15 to 70 percent by weight, to provide the extractable plasticizer to the blood which is placed in bag 12. It has been found that the desirable results of this invention can be achieved by this alternate technique. Insert 32 may be a single sheet, or a plurality of plastic beads, or any other convenient structure.

For example, the blood bag may be made out of a polyolefin such as polyethylene, polypropylene, the polyolefin block copolymer formulation described previously, polyester, polyurethane, or any other blood-compatible, inert, flexible plastic material. Insert 32, on the other hand, may be made of a blood-compatible polyvinyl chloride formulation and may contain most preferably up to about 50 percent of di-2-ethylhexylphthalate or di-2-ethylhexyladipate, to be extracted into the blood over the storage period. If desired, higher concentrations than 50 percent of the extractable plasticizer may be used in insert 32, since there is no need for insert 32 to exhibit a high tensile strength, as would be necessary if it were part of the bag wall itself. Correspondingly, the specific bag material chosen for use may be free of the extractable plasticizer, while the advantages of this invention are still achieved.

Accordingly, as blood is collected through the donor tube 16 into the blood bag 12, mixing with blood preservative 30 such as ACD or CPD solution in bag 12, the blood may then be processed or stored as desired. During storage, the presence of the plasticizer effectively suppresses the amount of plasma hemoglobin which is generated over a period of time, compared with blood stored in a bag made of a formulation which is free of blood-extractable plasticizers.

The blood may be centrifuged, with the red cells settling to the bottom of donor bag 12, and the plasma and other components being expressed through tubing 20 into transfer bags 24, 26. Thereafter, the expressed blood components are free from exposure to plasticizer, while the red cells in bag 12 may be stored with appropriate treatment to continue to receive the benefit of the presence of plasticizer in the material of transfer bag 12.

The materials from which transfer bags 24, 26 are made may also exhibit other benefits; for example, polyolefins and other materials may have improved gas transmission characteristics for improved platelet survival, since the carbon dioxide diffuses through the bag wall more readily than with polyvinyl chloride, with the result that the pH remains more stable.

Also, if desired, donor bag 12 and transfer bags 24, 26 may be separate bags that have been connected together during use by means of a sterile connector system, for example, that shown in U.S. Pat. No. 4,004,586, or any other sterile connector system.

The following examples are for illustrative purposes only, and are not intended to limit the invention described herein.

EXAMPLE 1

Blood bags were prepared of a design similar to the commercially available Fenwal donor bag, but made of a polyester as described in U.S. Pat. No. 4,045,431. The blood bags were sterilized in accordance with commercial standards, and while blood was drawn into the blood bags.

The first group of bags was made of the same polyester and was plasticizer-free, while the second group of bags was soaked to about a 20 weight percent concentration of di-2-ethylhexylphthalate plasticizer.

The blood was divided between first group and second group of bags in equal quantities in a conventional manner, and the bags were sealed off. Thereafter, the bags were stored at 4° C. for 21 days.

Then, the amount of plasma hemoglobin was measured in the two groups of bags, with the results as shown in Table I below.

TABLE I

| | | Plasma Hemoglobin (mg. %) | |
|---|---|---|---|
| | | First Group of Bags (plasticizer free) | Second Group of Bags Containing Plasticizer |
| Multiple Bag No. | 1 | 40.7 mg. % | 16.5 mg. % |
| | 2 | 36.7 | 21.3 |
| | 3 | 11.5 | 7.2 |
| | 4 | 21.1 | 9.4 |
| | 5 | 20.9 | 12.3 |
| | 6 | 42.6 | 9.8 |
| | 7 | 62.7 | 21.4 |
| | 8 | 34.0 | 18.4 |
| | 9 | 44.6 | 14.6 |
| | 10 | 31.8 | 9.7 |
| Average | | 34.7 | 14.1 |

The above data shows the significant reduction in plasma hemoglobin which results from storing whole blood for 21 days under conventional storage conditions in a blood bag which contains plasticizer, even when the plasticizer is not necessary for its usual purpose of obtaining desired characteristics in the plastic of the blood bag.

EXAMPLE 2

Blood bags were made out of the commercial polyvinyl chloride formulation utilized by Travenol Laboratories, Inc. and containing from 25 to 30 percent by weight of di-2-ethylhexylphthalate. Other blood bags were made out of different formulations as indicated in Table II below, and were essentially free of blood-extractable ester plasticizers.

Multiple samples of all of the blood bags were filled with whole blood and were stored for 21 days. Table II below illustrates the numbers of samples tested and the average amount of plasma hemoglobin expressed in terms of milligram percent for the various groups of sample bags.

TABLE II

| | No. of Samples Tested | Mean Amount of Plasma Hemoglobin (mg. %) |
|---|---|---|
| Commercial polyvinyl chloride blood bag formulation of Travenol Laboratories, Inc. | 21 | 20.4 |
| Polyvinyl chloride plasticized with tri-ethylhexyl mellitate | 10 | 51.7 |
| Polyolefin blend as described in Example 2 of the U.S. Pat. S.N. 819,924 cited above | 10 | 48.8 |
| Flexible polyester | 8 | 45.2 |
| Ethylene vinyl acetate copolymer | 4 | 43.2 |
| Polyethylene | 4 | 45.0 |

The above shows that the presence of the extractable ester plasticizer provides a substantial reduction in the creation of plasma hemoglobin in stored blood.

Suitable multiple blood bags may be made in accordance with this example, with the donor bag being made from the commercial Travenol polyvinyl chloride formulation, and the transfer bags being made of one or more of the remaining formulations described in Table II.

The above has been offered for illustrative purposes only, and is not intended to limit the invention of this application, which is as defined in the claims below.

That which is claimed is:

1. In a multiple blood bag system which comprises a first bag, a second bag, and conduit means providing sealed flow communication between said first bag and second bag in which said first bag is made of a plastic material which comprises a different polymer entity from that of said second bag, one of said bags being equipped with a blood collection tube, and the polymer entity of the the first bag exhibiting the characteristic of suppressing hemolysis of blood cells on long term storage, whereby the first bag and second bag exhibit differing physical characteristics which are selectively beneficial to their functions.

2. The multiple bag blood system of claim 1 in which a second transfer bag is present, being made of a translucent, flexible, sterilizable material which is free of blood-extractable plasticizers and exhibits a higher carbon dioxide diffusion characteristic than the other bags in the system whereby the pH of the platelets stored therein is resistant to reduction.

3. The multiple bag system of claim 1 in which said first bag is a donor bag for receiving whole blood from a donor, said blood collection tube being connected to the first bag, said second bag comprising a transfer bag for receiving a blood component from the donor bag.

4. The multiple bag system of claim 1 in which said first bag contains an amount of liquid plasticizer sufficient to suppress the amount of plasma hemoglobin produced by blood stored therein, when compared with a corresponding bag free of said plasticizer.

5. The multiple bag system of claim 1 in which said first bag contains an amount of an ester-type material which is sufficient to suppress the amount of plasma hemoglobin produced by blood stored therein, when compared with a corresponding bag free of said ester-type material.

6. The multiple bag system of claim 1 in which said first bag contains an ester-type plasticizer in a concentration sufficient to cause a reduction in the plasma hemoglobin content of blood stored in said bag for 21 days, when compared with a corresponding bag which is free of said material.

7. In a multiple blood bag system which comprises a first bag, a second bag, and conduit means providing sealed flow communication between said first and second bags, the improvement comprising: said second bag being made of a translucent, flexible, sterilizable material which is free of blood-extractable plasticizers, said first bag being made of a translucent, flexible, sterilizable material which contains an amount of liquid plasticizer selected from the group consisting of dioctylphthalates and dioctyladipates sufficient to suppress the amount of plasma hemoglobin produced by blood stored therein.

8. In a multiple blood bag system which comprises a donor bag for receiving blood from a donor, at least one transfer bag for receiving a blood component from said donor bag, and conduit means providing sealed, flow communication between said donor bag and transfer bag, the improvement comprising:

said transfer bag being made of a translucent, flexible, sterilizable material which is free of blood-extractable plasticizers, said donor bag being made of a translucent, flexible, sterilizable material which contains from 5 to 50 percent by weight of a diester selected from the group consisting of dioctylphthalates and dioctyladipates.

9. The blood bag system of claim 8 in which said liquid plasticizer is a diethylhexylphthalate.

10. In a multiple blood bag system which comprises a donor bag for receiving blood from a donor, at least one transfer bag for receiving a blood component from said donor bag, and conduit means providing sealed, flow communication between said donor bag and transfer bag, the improvement comprising:

said transfer bag being made of a translucent, flexible, sterilizable material, which is free of blood-extractable plasticizers, said donor bag being made of a translucent, flexible, sterilizable material which contains from 5 to 50 percent by weight of a diester selected from the group consisting of di-2-ethylhexylphthalate and di-2-ethylhexyladipate.

11. In a multiple blood bag system which comprises a donor bag for receiving blood from a donor, at least one transfer bag for receiving a blood component from said donor bag, and conduit means providing sealed, flow communication between said donor bag and transfer bag, the improvement comprising:

said transfer bag being made of a transparent, flexible, autoclavable material which is free of blood-extractable plasticizers, said donor bag being made of a transparent, flexible, autoclavable material which contains from 15 to 50 percent by weight of di-2-ethylhexylphthalate.

12. The multiple blood bag system of claim 11 in which said transfer bag is made of a polyolefin material.

13. The multiple blood bag system of claim 12 in which said donor bag is made of a polyester material.

14. The multiple blood bag system of claim 12 in which said donor bag is made of a formulation of polyvinyl chloride plasticized with said di-2-ethylhexyl phthalate.

15. The multiple blood bag system of claim 12 in which said donor bag contains from 15 to 40 percent by weight of di-2-ethylhexyl phthalate.

16. The multiple blood bag system of claim 12 in which said conduit means comprises flexible tubing made of the same translucent, flexible autoclavable material as the transfer bag.

17. The multiple blood bag system of claim 12 in which a plurality of transfer bags are present, being in communication through said conduit means with the donor bag.

18. The multiple blood bag system of claim 12 in which at least one of said transfer bags is made of a copolymer comprising from 10 to 40 percent by weight of a polyolefin consisting essentially of propylene units; from 40 to 85 percent by weight of a block copolymer, having thermoplastic rubber characteristics, consisting essentially of (1) a central block comprising 50 to 85 percent by weight of the copolymer molecule, of a rubbery olefin polymer of generally equal proportions of ethylene and butylene units, and (2) terminal blocks of polystyrene; and from 0 to 40 percent by weight of a softening agent selected from the group consisting of polyethylene and poly(ethylene-vinyl acetate) containing no more than 35 percent by weight of vinyl acetate.

19. The multiple blood bag system of claim 18 in which a second transfer bag is present which is made of a flexible polyester material, and said donor bag is made of polyvinyl chloride plasticized with said di-2-ethylhexylphthalate.

20. The multiple blood bag system of claim 11 in which said transfer bag is made of a polyolefin material which exhibits a relatively high low-temperature strength, whereby the bag may be frozen for collection of cryoprecipitate.

21. In a multiple blood bag system which comprises a donor bag for receiving blood from a donor, at least one transfer bag for receiving a blood component from said donor bag, and conduit means providing sealed, flow communication between said donor bag and transfer bag, the improvement comprising: said transfer bag being made of a translucent, flexible, sterilizable polyolefin material which is free of blood-extractable plasticizers and exhibits a relatively high carbon dioxide diffusion characteristic whereby the pH of platelets stored therein is resistent to reduction, said donor bag being made of a translucent, flexible, sterilizable plastic material which contains from 15 to 50 percent by weight of a blood-extractable plasticizer selected from the group consisting of dioctylphthalates and dioctyladipates.

22. The multiple blood bag system of claim 21 in which said extractable plasticizer is di-2-ethylhexylphthalate.

23. The multiple blood bag system of claim 22 in which said donor bag is made of a polyvinyl chloride formulation plasticized with di-2-ethylhexylphthalate.

24. In a multiple blood bag system which comprises a donor bag for receiving blood from a donor, at least one transfer bag for receiving a blood component from said donor bag, and conduit means providing sealed, flow communication between said donor bag and transfer bag, the improvement comprising: said transfer bag being made of a translucent, flexible, sterilizable, polyester material, free of ester-type blood extractable materials, said donor bag being made of a translucent, flexible, sterilizable, polyvinyl chloride plastic material which contains from 5 to 50 percent by weight of di-2-ethylhexylphthalate.

25. In a multiple blood bag system which comprises a donor bag for receiving blood from a donor, at least one transfer bag for receiving a blood component from said donor bag, and conduit means providing sealed, flow communication between said donor bag and transfer bag, the improvement comprising: said transfer bag being made of a translucent, flexible, sterilizable material which is free of blood-extractable plasticizer, said donor bag being made of a translucent, flexible, sterilizable plastic material, said donor bag containing in its interior an insert portion of plastic material which contains at least 5 percent by weight of a blood-extractable plasticizer selected from the group consisting of dioctylphthalates and dioctyladipates.

26. The multiple blood bag system of claim 25 in which 15 to 50 percent by weight of said blood extractable plasticizer is present in said interior plastic insert.

27. The multiple blood bag system of claim 26 in which the outer walls of said donor bag are essentially free of blood extractable plasticizers.

28. The multiple blood bag system of claim 26 in which said interior plastic insert comprises a polyvinyl chloride formulation containing a blood-extractable plasticizer.

29. In a multiple blood bag system which comprises a donor bag for receiving blood from a donor, at least one transfer bag for receiving a blood component from said donor bag, and conduit means providing sealed, flow communication between said donor bag and transfer bag, the improvement comprising:

said transfer bag being made of a translucent, flexible, sterilizable material which is free of blood-extractable plasticizers, said donor bag being made of a translucent, flexible, sterilizable material which contains sufficient amount of an ester material selected from the group consisting of dioctylphthalates and dioctyladipates to cause a reduction in the plasma hemoglobin content of blood stored in said bag for 21 days, when compared with a corresponding bag which is free of said material.

30. The blood bag system of claim 29 in which said ester material contains branched octyl radicals.

31. The blood bag system of claim 30 in which said ester material is di-2-ethylhexylphthalate.

32. The multiple blood bag system of claim 29 in which said transfer bag is made of a polyolefin material.

33. The multiple blood bag system of claim 32 in which said donor bag is made of a polyester material.

34. The multiple blood bag system of claim 33 in which said donor bag is made of a formulation of polyvinyl chloride plasticized with said di-2-ethylhexylphthalate.

35. The multiple blood bag system of claim 34 in which a plurality of transfer bags are present, being in communication through said conduit means with the donor bag.

36. The multiple blood bag system of claim 29 in which at least one of said transfer bags is made of a copolymer comprising from 10 to 40 percent by weight of a polyolefin consisting essentially of propylene units; from 40 to 85 percent by weight of a block copolymer, having thermoplastic rubber characteristics, consisting essentially of (1), a central block comprising 50 to 85 percent by weight of a copolymer molecule, of a rubbery olefin polymer of generally equal proportions of ethylene and butylene units and (2) terminal blocks of polystyrene; and from 0 to 40 percent by weight of a softening agent selected of the group consisting of polyethylene and poly(ethylene-vinyl acetate) containing no more than 35 percent by weight of vinyl acetate.

37. The multiple bag system of claim 36 in which a second transfer bag is present which is made of a flexible polyester material, and said donor bag is made of polyvinyl chloride which contains di-2-ethylhexylphthalate.

* * * * *

US004222379B1

REEXAMINATION CERTIFICATE (1696th)

United States Patent [19]

Smith

[11] B1 4,222,379

[45] Certificate Issued May 12, 1992

[54] MULTIPLE BLOOD BAG HAVING PLASTICIZER-FREE PORTIONS HIGH BLOOD COMPONENT SURVIVAL RATE

[75] Inventor: Dale A. Smith, Barrington, Ill.

[73] Assignee: Baxter Travenol Laboratores, Inc., Deerfield, Ill.

Reexamination Request:
No. 90/001,356, Oct. 16, 1987

Reexamination Certificate for:

| | |
|---|---|
| Patent No.: | 4,222,379 |
| Issued: | Sep. 16, 1980 |
| Appl. No.: | 955,059 |
| Filed: | Oct. 26, 1978 |

[51] Int. Cl.[5] ............ A61M 5/00; A61J 1/10
[52] U.S. Cl. ............ 604/410
[58] Field of Search ............ 604/403-416

[56] References Cited

U.S. PATENT DOCUMENTS

| | | | |
|---|---|---|---|
| 3,186,961 | 6/1975 | Sears | 260/30.4 |
| 3,940,802 | 3/1976 | Sako | 3/1.4 |
| 3,945,380 | 3/1976 | Dabney et al. | 604/410 |
| 3,986,506 | 10/1976 | Garber et al. | 604/410 |
| 4,112,989 | 9/1978 | Grode et al. | 604/408 |
| 4,140,162 | 2/1979 | Gajewski et al. | 150/1 |
| 4,451,259 | 5/1984 | Geissler et al. | 604/408 |

FOREIGN PATENT DOCUMENTS 51-50387 of 1976 Japan .
1587522 12/1981 United Kingdom .

OTHER PUBLICATIONS

"Development of Containers for Preservation of Frozen Blood Components", Becker, Prepared by Travenol Laboratories, Inc., Oct. 1969.
"Reduction of Haemolysis During Perfusion by Collection and Storage of Blood in Plastic Bags", Snow et al., Lancet, Jul. 16, 1960.
"Fundamentals of Developments of Medicine", vol. XII, No. 12, p. 224.

*Primary Examiner*—James C. Housel

[57] ABSTRACT

A multiple blood bag system comprising a donor bag for receiving blood from a donor, and one or more transfer bags, communicating by flexible tubing with the donor bag, for receiving a blood component from the donor bag. In accordance with this invention, the various bags may be made of differing materials to provide differing characteristics to the bags as desired. For example, the transfer bag or bags may be made of a translucent, flexible, sterilizable material which is free of blood extractable ester-type plasticizers, and may have a relatively high carbon dioxide diffusion capacity. The donor bag may be made of a translucent, flexible, sterilizable material which contains preferably at least five percent by weight of a specified ester plasticizer, sufficient to cause a substantial reduction in plasma hemoglobin produced by blood stored under normal conditions for 21 days in the donor bag, when compared with blood in a corresponding, plasticizer-free donor bag stored under equivalent conditions.

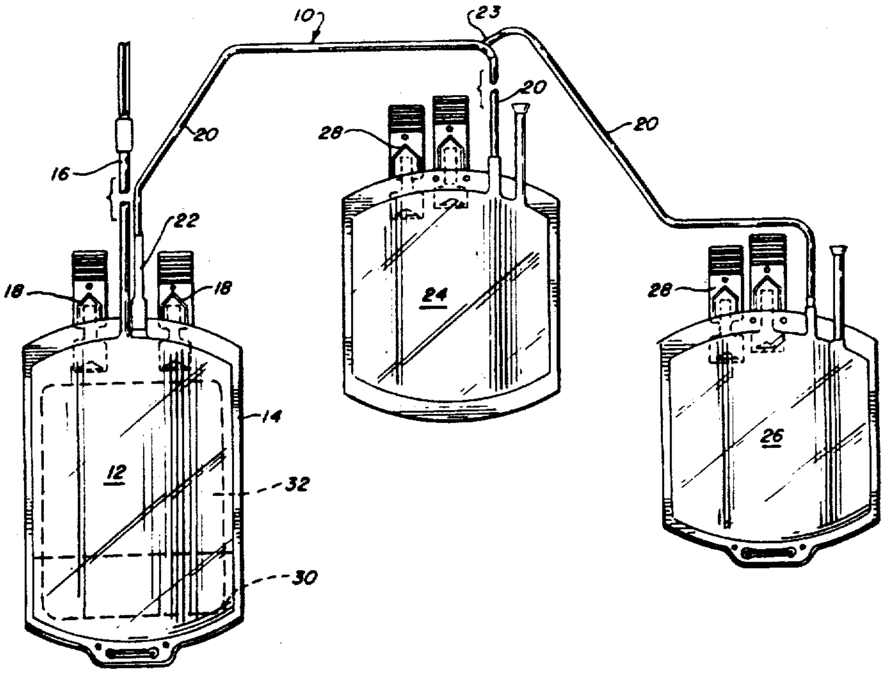

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 25-28 is confirmed.

Claims 1-24 and 29-37 are cancelled.

* * * * *